(12) United States Patent
Gopalsamy et al.

(10) Patent No.: US 6,525,061 B1
(45) Date of Patent: Feb. 25, 2003

(54) METHODS FOR THE SOLID PHASE SYNTHESIS OF 2-AMINO-4(H)-QUINAZOLINONE DERIVATIVES

(75) Inventors: Ariamala Gopalsamy, Mahwah, NJ (US); Hui Y. Yang, New City, NY (US)

(73) Assignee: Wyeth, Madison, NJ (US)

( * ) Notice: Subject to any disclaimer, the term of this patent is extended or adjusted under 35 U.S.C. 154(b) by 31 days.

(21) Appl. No.: 09/711,795

(22) Filed: Nov. 10, 2000

Related U.S. Application Data

(60) Provisional application No. 60/240,950, filed on Nov. 16, 1999.

(51) Int. Cl.[7] ................. A61K 31/517; C07D 239/95
(52) U.S. Cl. .................. 514/266.3; 514/267; 544/249; 544/287
(58) Field of Search ................ 544/249, 287; 514/266.3, 267

(56) References Cited

PUBLICATIONS

Erb et al., Chemical Abstracts, vol. 133:120304, 2000.*
El–Reedy et al., Chemical Abstracts, vol. 114:42705, 1991.*
Klopman et al., Chemical Abstracts, vol. 110:150323, 1989.*
DeRuiter et al., J. Med. Chem., 29, 627–629 (1986).
Hussain et al., Pharmaceuticals Research, 5, 242–244 (1988).
Hess et al., J. Med. Chem., 11, 130–136 (1968).
Borman, S., Chemical & Engineering News, 75 (8), 43–62 (1997).
Coopla, G.M., J. Org. Chem., 41, 825–831 (1976).

* cited by examiner

*Primary Examiner*—Richard L. Raymond
(74) *Attorney, Agent, or Firm*—Rebecca R. Barrett

(57) ABSTRACT

The present invention relates to solid phase synthesis of substituted 2-amino-4(H)-quinazolinone compounds of formula (I):

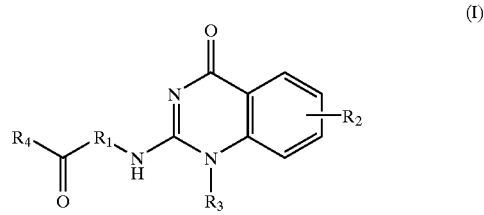

having pharmacological activity, to processes for their preparation, to a combinatorial library and solid phase methods for preparing libraries of the compounds, to utilizing libraries of the compounds for drug discovery, and to pharmaceutical compositions thereof.

3 Claims, No Drawings

METHODS FOR THE SOLID PHASE SYNTHESIS OF 2-AMINO-4(H)-QUINAZOLINONE DERIVATIVES

This application claims the benefit of U.S. Provisional Application No. 60/240,950, filed Nov. 16, 1999.

FIELD OF THE INVENTION

The present invention relates to substituted 2-amino-1,4-dihydroquinazolin-4-one derivatives having pharmacological activity, to processes for their preparation, to combinatorial and solid phase methods for preparing libraries of the compounds, to utilizing libraries of the compounds for drug discovery, and to pharmaceutical compositions thereof.

BACKGROUND OF THE INVENTION

Quinazolinone derivatives are important class of molecules with physiological significance and pharmaceutical utility. Substituted quinazolinones are a useful class of compounds. DeRuiter, et al. (*J. Med. Chem.* 1986, 29, 627–629) describe 2-(arylamino)-4(3H)-quinazolinones as inhibitor of enzyme aldose reductase that prevents or delays the onset of diabetic complications. Hussain, et al. (*Pharmaceuticals Research,* 1988, 5, 242–244) and Hess, et al. (*J. Med. Chem.* 1968, 11, 130–136) describe antihypertensive activity of 2-amino-4(3H)-quinazolinone.

Combinatorial chemistry is becoming an important tool for drug discovery and lead optimization (Borman, S. *Chemical and Engineering News* 1997, 75 (8), 43–62). A combinatorial synthesis requires that at least two components of the product molecules be independently variable, so that all of the combinations of these components can be prepared. Thus, to prepare a combinatorial library of quinazolinones with a high degree of potential diversity and wide utility for drug discovery using solid phase techniques, it is important to identify a synthesis in which all the components can be independently varied. The solution phase synthesis of 2-aminoquinazolinones by condensation of thiopseudoureas and isotoic anhydrides is known (Coopla, G. M. *J. Org. Chem.* 1976, 41, 825). For a solid phase combinatorial synthesis it is necessary to modify this syntheses to allow for the independent introduction of variables and to adapt the solution phase synthesis to a solid supported synthesis. The solid phase 2-aminoquinazolinone synthesis of this invention is achieved by using a variety of amino acids as starting material which can be attached to a solid support through the carboxylic acid group.

Multiple compounds can be prepared simultaneously by the solid phase process. The simultaneous solid phase synthesis of a library of trisubstituted quinazolinones of the present invention is not known. The preparation of libraries of compounds of the present invention is useful because it provides rapid structural variation and structure-activity information.

The libraries of substituted quinazolinones synthesized according to the present invention are useful for drug discovery.

Accordingly, the present invention provides compounds of the formula (I):

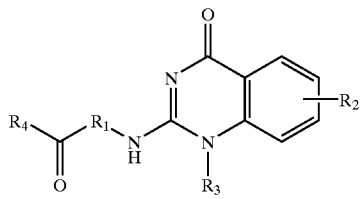

wherein:
$R^1$ is phenyl optionally substituted with chloro, bromo, fluoro, straight chain alkyl of 1 to 6 carbon atoms, branched chain alkyl of 2 to 6 carbon atoms, or alkoxy of 1 to 6 carbon atoms, straight chain alkyl of 1 to 6 carbon atoms optionally substituted with hydroxyl, amino, guanidino, thiol, phenyl, substituted phenyl, COOH, or CONH2, branched chain alkyl of 3 to 7 carbon atoms, optionally substituted with optionally substituted with hydroxyl, amino, guanidino, thiol, phenyl, substituted phenyl, COOH, or CONH2;

$R^2$ is hydrogen, fluoro, chloro, bromo, nitro, straight chain alkyl of 1 to 6 carbon atoms, branched chain alkyl of 3 to 7 carbon atoms, cycloalkyl of 3 to 7 carbon atoms, phenyl or phenyl substituted with fluoro, chloro, bromo, straight chain alkyl of 1 to 6 carbon atoms, branched chain alkyl of 3 to 7 carbon atoms, cycloalkyl of 3 to 7 carbon atoms, alkoxy of 1 to 6 carbon atoms, or methylenedioxy;

$R^3$ is hydrogen, straight chain alkyl of 1 to 6 carbon atoms, branched chain alkyl of 3 to 7 carbon atoms, cycloalkyl of 3 to 7 carbon atoms, straight chain alkenyl of 2 to 6 carbon atoms, branched chain alkenyl of 3 to 9 carbon atoms, straight chain alkynyl of 3 to 9 carbon atoms, branched chain alkynyl of 4 to 9 carbon atoms, phenylalkyl of 7 to 12 carbon atoms, phenyl or acyl; and $R^4$ is hydroxy, alkoxy of 1 to 6 carbon atoms or amino; and pharmaceutical salts thereof.

In some preferred embodiments of the present invention R1 is phenyl and R4 is hydroxy.

Most preferred compounds of the present invention are:
4-[(4-oxo-1,4-dihydroquinazolin-2-yl)amino]benzoic acid,
4-[(1-methyl-4-oxo-1,4-dihydroquinazolin-2-yl)amino] benzoic acid,
4-[(1-allyl-4-oxo-1,4-dihydroquinazolin-2-yl)amino] benzoic acid,
4-[(1-benzyl-4-oxo-1,4-dihydroquinazolin-2-yl)amino] benzoic acid,
4-[(6-chloro-4-oxo-1,4-dihydroquinazolin-2-yl)amino] benzoic acid,
4-[(6-bromo-4-oxo-1,4-dihydroquinazolin-2-yl)amino] benzoic acid,
4-[(6-nitro-4-oxo-1,4-dihydroquinazolin-2-yl)amino] benzoic acid,
3-[(4-oxo-1,4-dihydroquinazolin-2-yl)amino]benzoic acid,
3-[(1-methyl-4-oxo-1,4-dihydroquinazolin-2-yl)amino] benzoic acid,
3-[(1-allyl-4-oxo-1,4-dihydroquinazolin-2-yl)amino] benzoic acid,
3-[(1-benzyl-4-oxo-1,4-dihydroquinazolin-2-yl)amino] benzoic acid,
3-[(6-chloro-4-oxo-1,4-dihydroquinazolin-2-yl)amino] benzoic acid,
3-[(6-bromo-4-oxo-1,4-dihydroquinazolin-2-yl)amino] benzoic acid, 3-[(6-nitro-4-oxo-1,4-dihydroquinazolin-2-yl)amino]
  benzoic acid,
N-(4-oxo-1,4-dihydroquinazolin-2-yl)-beta-alanine,
N-(1-methyl-4-oxo-1,4-dihydroquinazolin-2-yl)-beta-
  alanine,
N-(1-allyl-4-oxo-1,4-dihydroquinazolin-2-yl)-beta-alanine,
N-(1-benzyl-4-oxo-1,4-dihydroquinazolin-2-yl)-beta-
  alanine,
N-(6-chloro-4-oxo-1,4-dihydroquinazolin-2-yl)-beta-
  alanine,
N-(6-bromo-4-oxo-1,4-dihydroquinazolin-2-yl)-beta-
  alanine,
N-(6-nitro-4-oxo-1,4-dihydroquinazolin-2-yl)-beta-alanine,
4-[(1-allyl-4-oxo-1,4-dihydroquinazolin-2-yl)amino]-2-
  chlorobenzoic acid, and
5-[(1-allyl-4-oxo-1,4-dihydroquinazolin-2-yl)amino]-2-
  chlorobenzoic acid.

Compounds of the present invention are expected to be useful to delay the onset of diabetic complications such as cataract formation, retinopathy and neuropathy.

Compounds of Formula I may be prepared via solid phase synthesis which comprises the steps of:

a) attaching a Fmoc protected amino acid of the formula:

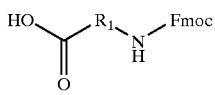

to a solid support to produce compounds of formula (1):

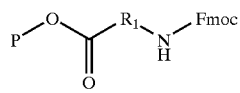

(1)

wherein P is a solid support;

b) Deprotecting said compounds of formula (1) with piperidine to produce compounds of formula (2):

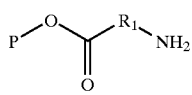

(2)

c) reacting said compounds of formula (2) with Fmoc-isothiocyanate to produce compounds of formula (3):

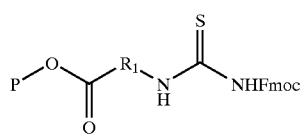

(3)

d) deprotecting said compounds of formula (3) with piperidine to produce compounds of formula (4):

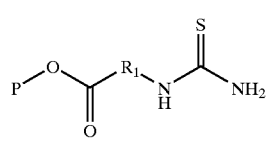

(4)

e) reacting said compounds of formula (4) with methyl iodide to produce compounds of formula (5):

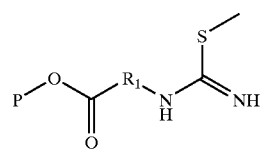

(5)

f) reacting said compounds of formula (5) with isotoic anhydrides of formula (6):

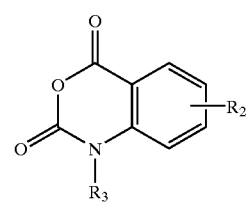

(6)

in polar aprotic solvent at ambient temperature to produce compounds of formula (7):

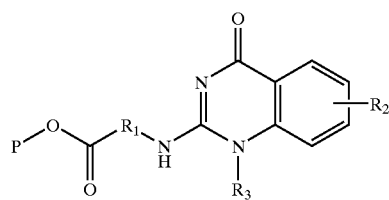

(7)

and g) reacting said compounds of formula (7) with a cleaving reagent such as trifluoroacetic acid to produce compounds of formula (I).

Libraries of compounds of Formula I can thus be prepared. Such libraries are useful for drug discovery by providing a group of quinazolinones with a high degree of diversity, thus allowing for structure-activity information against a given drug discovery target.

In accordance with the present invention, the solid support P is preferably a polystyrene resin crosslinked with divinylbenzene and functionalized with a linker such as a hydroxymethylphenoxy group. More preferably the solid support P is Wang's resin.

In some preferred embodiments of the present invention a substituted phenyl group has 1 to 3 substituents. More preferably, a substituted phenyl group has one substituent.

Substituted alkyl groups can have from 1 to three substituents. Substituted alkyl groups preferably have no more than one substitutent per carbon atom. Substituted alkyl groups preferably contains a total of from 1 to three substituents in some preferred embodiments of the invention.

Fmoc, as used herein refers to the protecting group, fluorenylmethoxycarbonyl.

It is understood that the definition of the compounds of formula (I), when $R^1$, $R^2$, $R^3$, and $R^4$ contain asymmetric carbons, encompasses all possible stereoisomers and mixtures thereof. In particular, it encompasses racemic modifications and any optical isomers. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Carboxylic acid salts of the compounds of this invention may be formed with bases such as alkali metals (Na, K, Li) or the alkaline earth metals (Ca or Mg).

The compounds of the pre sent invention may be prepared according to the general process outlined below in Scheme I.

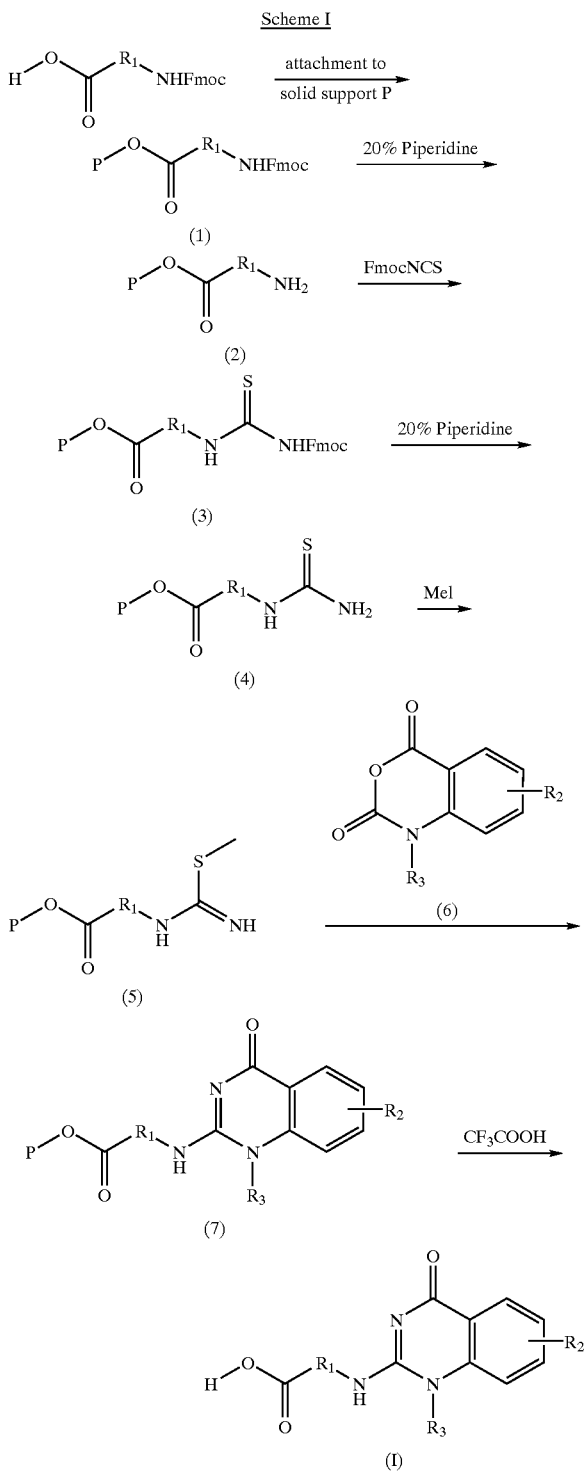

Thus, a Fmoc protected amino acid is attached to the preferred solid support P, a resin of polystyrene crosslinked with divinylbenzene and with a linker such as 4-hydroxymethylphenoxy, most preferably Wang's resin (Wang S.; *J. Am. Chem. Soc.* 1973, 95, 1328–1333) in the presence of a coupling reagent such as didiopropylcarbodiimide to produce a compound of formula (1). A compound of formula (1) is deprotected using 20% piperidine in DMF to produce a free amine of formula (2). Amine (2) is reacted with fluorenylmethyloxycarbonyl isothiocyanate (Kearney et al. *J. Org. Chem.* 1998, 63, 199) in methylene chloride to yield formula (3). Fmoc protecting group on formula (3) was deprotected using 20% piperidine in DMF to give the thiourea on a solid support of formula (4). Thiourea (4) is reacted with methyl iodide to produce a compound of formula (5). The compound of formula (5) is reacted with a isotoic anhydride of formula (6) in polar aprotic solvent like N,N-dimethylacetamide to produce a compound of formula (7). The compound of formula (I) wherein $R^1$, $R^2$, and $R^3$ are as defined above is removed from the solid support with an acidic cleavage mixture such as tritluoroacetic acid in dichloromethane.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patient suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and β-blocking agents.

The present invention further provides a compound of the invention for use as an active therapeutic substance and in particular can be used to delay the onset of diabetic complications such as cataract formation, retinopathy and neuropathy.

The following examples are illustrative and are not meant to be limiting of the present invention. Throughout the Examples, the following abbreviations are used.
Fmoc: 9-fluorenylmethoxycarbonyl
DMF: N,N-Dimethylformaide
HOBT: N-Hydroxybenzotriazole
DMAP: dimethylaminopyridine
DIC: N,N'-diisopropylcarbodiimide
MeOH: Methanol
DMSO: Dimethylsulfoxide
TFA: Trifluoroacetic acid

EXAMPLE 1

Preparation of 4-[(4-oxo-1,4-dihydroquinazolin-2-yl)amino]benzoic acid on Wang Resin Step 1: Fluorenylmethyloxycarbonyl Isothiocyanate The title compound was prepared from Fluorenylmethyloxycarbonyl chloride and potassium thiocyanate according to the procedure of Kearney et al. *J. Org. Chem.* 1998, 63, 199; $^1$H NMR (CDCl$_3$) $\delta$7.75 (d, J=7.5 Hz, 2H), 7.56 (d, J=7.5 Hz, 2H), 7.41 (t, J=7.5 Hz, 2H), 7.32 (t, J=7.5 Hz, 2H), 4.44 (d, J=7.4 Hz, 2H), 4.23 (t, J=7.4 Hz, 1H).

IR(cm$^{-1}$): 1963.32 (N=C=S stretch)

Step 2: Attachment of N-Fmoc-4-Aminobenzoic Acid to Wang Resin

Wang Resin (Wang, S. *J. Am. Chem. Soc.* 1973, 95, 1328–1333) (Ana Spec 100–200 mesh, 1% crosslinked; loading: 1.1 mmol/g; 5 g, 5.5 mmol) was swollen in anhydrous DMF (20 ml). A solution of N-Fmoc-4-Aminobenzoic acid (7.9 g, 22 mmol), HOBT (3.37 g, 22 mmol), DMAP (268.8 mg, 2.2 mmol) and DIC (3.4 ml, 22 mmol) in anhydrous DMF (30 ml) was added to the resin. The mixture was shaken at room temperature on an orbital shaker overnight. The mixture was filtered and the resin was washed with DMF (3×50 ml), MeOH (3×50 ml), CH$_2$Cl$_2$ (3×50 ml), and dried.

Step 3: Deprotection of Fmoc Group

The resin (5.5 mmol), prepared as described in step 2 above, was treated with a solution of 20% piperidine in DMF (2×50 ml, 10 min for the first time and 30 min for the second time) to remove the Fmoc protecting group from the resin. The mixture was filtered and the resin was washed with DMF (3×50 ml), MeOH (3×50 ml), and CH$_2$Cl$_2$ (3×50 ml).

Step 4: Reaction with Fmoc-isothiocyanate

To the 4-aminobenzoic acid on Wang resin (5.5 mmol) was added a solution of Fmoc-isothiocyanate (3.09 g, 11 mmol, prepared as described in step 1) in anhydrous CH$_2$Cl$_2$ (50 ml). After 20 min, the mixture was filtered, washed with CH$_2$Cl$_2$ (5×50 ml).

Step 5: Deprotection of Fmoc Group

The resin (5.5 mmol) obtained from step 4 was reacted again with a solution of 20% piperidine in DMF (2×50 ml, 10 min for the first time and 30 min for the second time) to produce the thiourea. The mixture was filtered and the resin was washed with DMF (3×50 ml), MeOH (3×50 ml), CH$_2$Cl$_2$ (3×50 ml), and dried.

To confirm that the reaction occured, 100 mg of resin was treated with 50% TFA/CH$_2$Cl$_2$ for 1 hr, filtered, and the filtrate was concentrated. MS [M+H]$^+$ m/z=197.

Step 6: Preparation of the Resin-bounded Methyl Thiourea

To the resin-bounded thiourea (5.5 mmol) in anhydrous DMF (50 ml) was added MeI (6.85 ml, 0.11 mol). After half an hour, the mixture was filtered and treated again with equal amount of MeI in DMF overnight. The mixture was then filtered and the resin was washed with DMF (3×50 ml), MeOH (3×50 ml), CH$_2$Cl$_2$ (3×50 ml), and dried.

To confirm that the reaction occured, 100 mg of resin was treated with 50% TFA/CH$_2$Cl$_2$ for 1 hr, filtered, and the filtrate was concentrated. MS [M+H]$^+$ m/z=211.

Step 7: Reaction with Isatoic Anhydride

A mixture of the resin (200 mg, 0.22 mmol; loading 1.1 mmol/g), prepared as described in step 6 and isatoic anhydride (85 mg, 1.1 mmol) in anhydrous N,N-dimethylacetamide was heated at 80° C. on the J-KEM block overnight. The mixture was then filtered and the resin was washed with DMF (3×50 ml), MeOH (3×50 ml), CH$_2$Cl$_2$ (3×50 ml), and finally cleaved from resin with 50% TFA/CH$_2$Cl$_2$ for 1 hr, filtered, and the filtrate was concentrated to give 4-[(4-oxo-1,4-dihydroquinazolin-2-yl)amino]benzoic acid; $^1$H NMR (DMSO-d$_6$) $\delta$7.27 (t, 1H), 7.48 (d, 1H), 7.68 (t, 1H), 7.85–7.95 (AB quartet, 4H), 7.99 (d, 1H), 9.04 (s, 1H), 10.90 (s, 1H), 12.65 (s, 1H).

EXAMPLE 2

Preparation of 4-[(1-methyl-4-oxo-1,4-dihydroquinazolin-2-yl)amino]benzoic acid on Wang Resin The resin product was prepared according to step 7 of example 1 from 4-aminobenzoic acid methyl isothiourea on Wang resin and N-methylisatoic anhydride.

A sample of resin was treated with 50% TFA/CH$_2$Cl$_2$ as in step 7 of example 1 to yield 4-[(1-methyl-4-oxo-1,4-dihydroquinazolin-2-yl)amino]benzoic acid; $^1$H NMR (DMSO-d$_6$) $\delta$3.45 (s, 3H), 7.40 (t, 1H), 7.46 (d, 1H), 7.65 (d, 1H), 7.84 (t, 1H), 7.95 (d, 2H), 8.03 (d, 2H), 10.30 (s, 1H), 12.70(s, 1H).

EXAMPLE 3

Preparation of 4-[(1-allyl-4-oxo-1,4-dihydroquinazolin-2-yl)amino]benzoic acid on Wang Resin The resin product was prepared according to step 7 of example 1 from 4-aminobenzoic acid methyl isothiourea on Wang resin and N-allylisatoic anhydride.

A sample of resin was treated with 50% TFA/CH$_2$Cl$_2$ as in step 7 of example 1 to yield 4-[(1-allyl-4-oxo-1,4-dihydroquinazolin-2-yl)amino]benzoic acid; $^1$H NMR (DMSO-d$_6$) $\delta$4.92 (m, 2H), 5.20 (m, 2H), 5.94–6.03 (m, 1H), 6.96 (t, 1H), 7.22 (d, 1H), 7.34 (d, 1H), 7.69 (t, 1H), 7.88 (d, 2H), 7.97 (d, 2H), 10.35 (s, 1H), 12.70(s, 1H).

EXAMPLE 4

Preparation of 4-[(1-benzyl-4-oxo-1,4-dihydroquinazolin-2-yl)amino]benzoic acid on Wang Resin The resin product was prepared according to step 7 of example 1 from 4-aminobenzoic acid methyl isothiourea on Wang resin and N-benzylisatoic anhydride.

A sample of resin was treated with 50% TFA/CH$_2$Cl$_2$ as in step 7 of example 1 to yield 4-[(1-benzyl-4-oxo-1,4-dihydroquinazolin-2-yl)amino]benzoic acid; $^1$H NMR (DMSO-d$_6$) $\delta$5.56 (s, 2H), 7.18–7.37 (m, 8H), 7.60 (t, 1H), 7.88 (d, 2H), 7.97 (d, 2H), 10.45 (s, 1H), 12.60(s, 1H).

EXAMPLE 5

Preparation of 4-[(6-chloro-4-oxo-1,4-dihydroquinazolin-2-yl)amino]benzoic acid on Wang Resin The resin product was prepared according to step 7 of example 1 from 4-aminobenzoic acid methyl isothiourea on Wang resin and 5-chloroisatoic anhydride.

A sample of resin was treated with 50% TFA/CH$_2$Cl$_2$ as in step 7 of example 1 to yield 4-[(6-chloro-4-oxo-1,4-dihydroquinazolin-2-yl)amino]benzoic acid; $^1$H NMR (DMSO-d,) $\delta$7.50 (d, 1H), 7.72 (dd, 1H), 7.85–7.95(m, 5H), 9.60 (s, 1H), 11.20(s, 1H), 12.70 (s, 1H).

EXAMPLE 6

Preparation of 4-[(6-bromo-4-oxo-1,4-dihydroquinazolin-2-yl)amino]benzoic acid on Wang Resin The resin product was prepared according to step 7 of example 1 from 4-aminobenzoic acid methyl isothiourea on Wang resin and 5-bromoisatoic anhydride.

A sample of resin was treated with 50% TFA/CH$_2$Cl$_2$ as in step 7 of example 1 to yield 4-[(6-bromo-4-oxo-1,4-dihydroquinazolin-2-yl)amino]benzoic acid; $^1$H NMR (DMSO-d$_6$) δ7.43 (d, 1H), 7.82 (dd, 1H), 7.85–7.94(AB quartet, 4H), 8.04 (d, 1H), 9.70 (s, 1H), 11.40 (s, 1H), 12.70 (s, 1H).

EXAMPLE 7

Preparation of 4-[(6-nitro-4-oxo-1,4-dihydroquinazolin-2-yl)amino]benzoic acid on Wang Resin The resin product was prepared according to step 7 of example 1 from 4-aminobenzoic acid methyl isothiourea on Wang resin and 5-nitroisatoic anhydride.

A sample of resin was treated with 50% TFA/CH$_2$Cl$_2$ as in step 7 of example 1 to yield 4-[(6-nitro-4-oxo-1,4-dihydroquinazolin-2-yl)amino]benzoic acid; $^1$H NMR (DMSO-d$_6$) δ7.60 (d, 1H), 7.86–7.98(AB quartet, 4H), 8.43(dd, 1H), 8.70(d, 1H), 9.46 (s, 1H), 11.48 (s, 1H), 12.72 (s, 1H).

EXAMPLE 8

Preparation of 4-[(1-allyl-4-oxo-1,4-dihydroquinazolin-2-yl)amino]-2-chlorobenzoic acid on Wang Resin The resin product was prepared according to step 7 of example 1 from 2-chloro-4-aminobenzoic acid methyl isothiourea on Wang resin and N-allylisatoic anhydride.

A sample of resin was treated with 50% TFA/CH$_2$Cl$_2$ as in step 7 of example 1 to yield 4-[(1-allyl-4-oxo-1,4-dihydroquinazolin-2-yl)amino]-2-chlorobenzoic acid; $^1$H NMR (DMSO-d$_6$) δ4.89 (m, 2H), 5.09–5.22 (dd, 2H), 5.92–6.02(m, 1H), 7.21(t, 1H), 7.33(d, 1H), 7.65–7.73(m, 2H), 7.79(d, 1H), 7.98(dd, 1H), 8.10(t, 1H), 8.73 (s, 1H), 11.60 (s, 1H), 12.90 (s, 1H).

EXAMPLE 9

Preparation of 5-[(1-allyl-4-oxo-1,4-dihydroquinazolin-2-yl)amino]-2-chlorobenzoic acid on Wang Resin The resin product was prepared according to step 7 of example 1 from 2-chloro-5-aminobenzoic acid methyl isothiourea on Wang resin and N-allylisatoic anhydride.

A sample of resin was treated with 50% TFA/CH$_2$Cl$_2$ as in step 7 of example 1 to yield 5-[(1-allyl-4-oxo-1,4-dihydroquinazolin-2-yl)amino]-2-chlorobenzoic acid; $^1$H NMR (DMSO-d$_6$) δ4.92 (m, 2H), 5.10–5.27 (dd, 2H), 5.97–6.07 (m, 1H), 7.32(t, 1H), 7.41(d, 1H), 7.51(d, 1H), 7.58(m, 1H), 7.75(t, 1H), 8.00 (d, 2H), 8.90 (s, 1H), 11.70 (s, 1H), 13.20 (s, 1H).

EXAMPLE 10

Preparation of 3-[(1-allyl-4-oxo-1,4-dihydroquinazolin-2-yl)amino]benzoic acid on Wang Resin The resin product was prepared according to step 7 of example 1 from 3-aminobenzoic acid methyl isothiourea on Wang resin and N-allylisatoic anhydride.

A sample of resin was treated with 50% TFA/CH$_2$Cl$_2$ as in step 7 of example 1 to yield 3-[(1-allyl-4-oxo-1,4-dihydroquinazolin-2-yl)amino]benzoic acid; $^1$H NMR (DMSO-d$_6$) δ4.95 (m, 2H), 5.14–5.28 (dd, 2H), 5.97–6.07 (m, 1H), 7.30(t, 1H), 7.43–7.49(m, 2H), 7.71–7.77(m, 2H), 7.93–8.02(m, 3H), 8.87 (s, 1H), 11.60 (s, 1H), 13.10 (s, 1H)

EXAMPLE 11

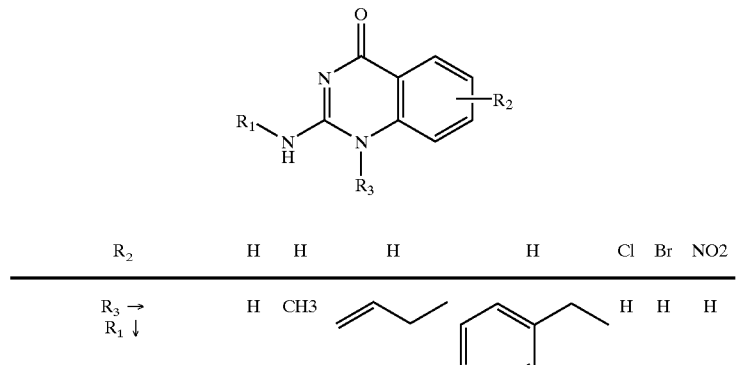

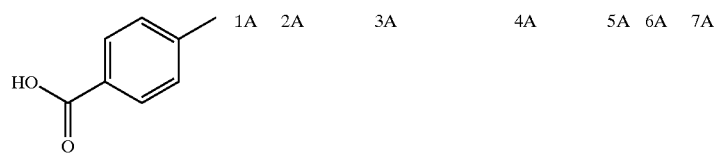

-continued

Parallel Synthesis of Twenty One Compounds

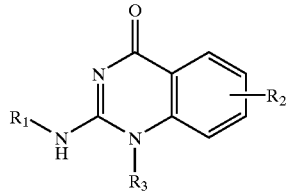

| R₂ | H | H | H | H | Cl | Br | NO2 |
|---|---|---|---|---|---|---|---|
| (3-methylbenzoic acid) | 1B | 2B | 3B | 4B | 5B | 6B | 7B |
| (butyric acid) | 1C | 2C | 3C | 4C | 5C | 6C | 7C |

Twenty one compounds were synthesized in parallel with twenty one scintillation vials arranged in a 3×7 matrix. One of each of the resins prepared according to the procedure outlined in Example 1 was placed in seven scintillation vials in one row (200 mg per vial, 0.22 mmol; loading 1.1 mmol/g): 4-aminobenzoic acid on Wang resin in row 1; 3-aminobenzoic acid on Wang resin in row 2; β-alanine on Wang resin in row 3. To each vial was added isatoic anhydride in anhydrous N,N-dimethylacetamide: isatoic anhydride in column 1; N-methylisatoic anhydride in column 2; N-allylisatoic anhydride in column 3; N-benzylisatoic anhydride in column 4; 5-chloroisatoic anhydride in column 5; 5-bromoisatoic anhydride in column 6; 5-nitroisatoic anhydride in column 7. The reaction vials were then placed in a J-KEM block and rotated at 80° C. overnight. The reaction mixtures were transferred into twenty one filtration vessels in a multiple peptide synthesizer. The mixtures were filtered and the resin in each vessel was washed with dimethylformamide (3×4 ml), methanol (3×4 ml), dichloromethane (3×4 ml), and dried.

The 21 products were cleaved from the solid support for characterization according to the following procedure. To each vessel was added 1:1 trifluoroacetic acid/dichloromethane (4 ml). The synthesizer was left standing for 1 h, and the solution were filtered into 1 dram vials. The resin in each vessel was washed with dichloromethane (2 ml). The solutions were concentrated under a nitrogen stream and dried in Savant under vacuum. The characterization data are listed in the following table.

Solid Phase Synthesis of 2-Amino-1,4-dihydroquinazolin-4-one Derivatives

| Entry | R₁ | R₃ | R₂ | LC (min) MS (M + H) | Yield (mg) |
|---|---|---|---|---|---|
| 1A | 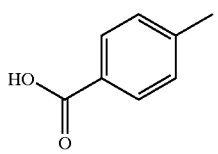 | H | H | 2.250 282.0 | 11.9 |

-continued
Solid Phase Synthesis of 2-Amino-1,4-dihydroquinazolin-4-one Derivatives
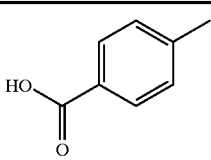
| Entry | R₁ | R₃ | R₂ | LC (min) MS (M + H) | Yield (mg) |
|---|---|---|---|---|---|
| 2A | 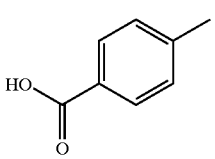 | CH₃ | H | 1.937 296.0 | 12.8 |
| 3A |  | 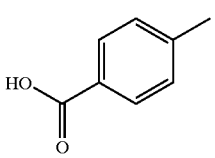 | H | 2.412 322.0 | 12.7 |
| 4A |  | 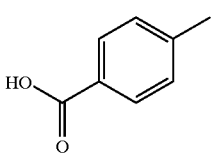 | H | 2.106 372.1 | 13.9 |
| 5A | 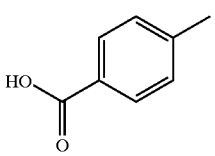 | H | Cl | 2.185 316.0 | 12.7 |
| 6A | 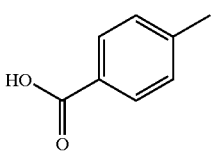 | H | Br | 2.300 360.0 | 14.9 |
| 7A | 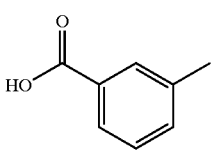 | H | NO₂ | 2.059 327.0 | 17.1 |
| 1B | 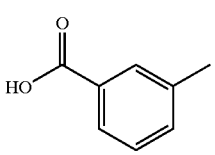 | H | H | 2.103 282.0 | 32.7 |
| 2B | 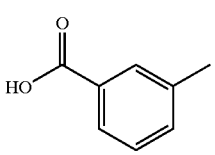 | CH₃ | H | 1.781 296.0 | 35.9 |

-continued
Solid Phase Synthesis of 2-Amino-1,4-dihydroquinazolin-4-one Derivatives
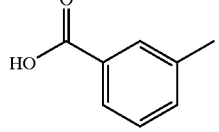
| Entry | R$_1$ | R$_3$ | R$_2$ | LC (min) MS (M + H) | Yield (mg) |
|---|---|---|---|---|---|
| 3B | 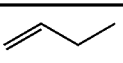 | 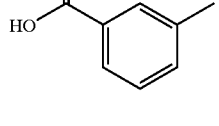 | H | 2.196 322.1 | 36.1 |
| 4B | 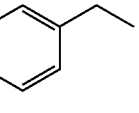 | 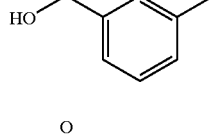 | H | 2.847 372.1 | 40.5 |
| 5B | 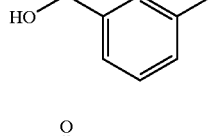 | H | Cl | 2.129 316.0 | 32.9 |
| 6B | 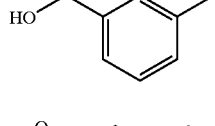 | H | Br | 2.209 362.0 | 37.1 |
| 7B | 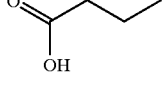 | H | NO$_2$ | 2.054 327.0 | 30.6 |
| 1C | 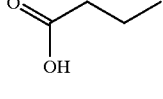 | H | H | 1.114 234.1 | 30.7 |
| 2C | 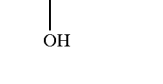 | CH$_3$ | H | 1.135 248.1 | 31.8 |
| 3C | 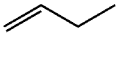 | 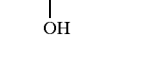 | H | 1.601 274.1 | 33.2 |
| 4C | 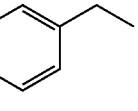 | 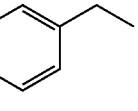 | H | 2.118 324.1 | 35.8 |

-continued

Solid Phase Synthesis of 2-Amino-1,4-dihydroquinazolin-4-one Derivatives

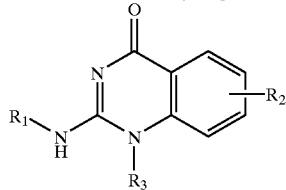

| Entry | $R_1$ | $R_3$ | $R_2$ | LC (min) MS (M + H) | Yield (mg) |
|---|---|---|---|---|---|
| 5C | O=C(OH)CH₂CH₂CH₂– | H | Cl | 1.809 268.0 | 34.9 |
| 6C | O=C(OH)CH₂CH₂CH₂– | H | Br | 1.911 312.0 | 38 |
| 7C | O=C(OH)CH₂CH₂CH₂– | H | NO₂ | 1.964 279.0 | 47.2 |
| Ex. 8 | 2-Cl-4-Me-benzoic acid | allyl | H | 2.744 356.0 | 17.4 |
| Ex. 9 | 2-Cl-5-Me-benzoic acid | allyl | H | 2.430 356.0 | 37.2 |

We claim:
1. A compound having the formula:

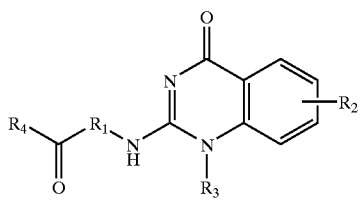

wherein:
$R^1$ is phenyl optionally substituted with chloro, bromo, fluoro, straight chain alkyl of 1 to 6 carbon atoms, branched chain alkyl of 2 to 6 carbon atoms, or alkoxy of 1 to 6 carbon atoms,
  straight chain alkyl of 1 to 6 carbon atoms optionally substituted with hydroxyl, amino, guanidino, thiol, phenyl, substituted phenyl, COOH, or CONH2, or branched chain alkyl of 3 to 7 carbon atoms, optionally substituted with hydroxyl, amino, guanidino, thiol, phenyl, substituted phenyl, COOH, or CONH2;
$R^2$ is hydrogen, fluoro, chloro, bromo, nitro, straight chain alkyd of 1 to 6 carbon atoms, branched chain alkyl of 3 to 7 carbon atoms, cycloalkyl of 3 to 7 carbon atoms, phenyl or phenyl substituted with fluoro, chloro, bromo, straight chain alkyl of 1 to 6 carbon atoms, branched chain alkyl of 3 to 7 carbon atoms, cycloalkyl of 3 to 7 carbon atoms, alkoxy of 1 to 6 carbon atoms, or methylenedioxy;
$R^3$ is hydrogen, straight chain alkyl of 1 to 6 carbon atoms, branched chain alkyl of 3 to 7 carbon atoms, cycloalkyl of 3 to 7 carbon atoms, straight chain alkenyl of 2 to 6 carbon atoms, branched chain alkenyl of 3 to 9 carbon atoms, straight chain alkynyl of 3 to 9 carbon atoms, branched chain alkynyl of 4 to 9 carbon atoms, phenylalkyl of 7 to 12 carbon atoms, phenyl or acyl; and
$R^4$ is hydroxy, alkoxy of 1 to 6 carbon atoms or amino; and pharmaceutical salts thereof with the proviso that when $R^1$ is phenyl and $R^3$ is hydrogen, $R^2$ is not hydrogen.
2. A compound of claim 1 which is selected from the group consisting of
4-[(1-methyl-4-oxo-1,4-dihydroquinazolin-2-yl)amino] benzoic acid,
4-[(1-allyl-4-oxo-1,4-dihydroquinazolin-2-yl)amino] benzoic acid,
4-[(1-benzyl-4-oxo-1,4-dihydroquinazolin-2-yl)amino] benzoic acid, 4-[(6-chloro-4-oxo-1,4-dihydroquinazolin-2-yl)amino]benzoic acid,
4-[(6-bromo-4-oxo-1,4-dihydroquinazolin-2-yl)amino]benzoic acid,
4-[(6-nitro-4-oxo-1,4-dihydroquinazolin-2-yl)amino]benzoic acid,
3-[(1-methyl-4-oxo-1,4-dihydroquinazolin-2-yl)amino]benzoic acid,
3-[(1-allyl-4-oxo-1,4-dihydroquinazolin-2-yl)amino]benzoic acid,
3-[(1-benzyl-4-oxo-1,4-dihydroquinazolin-2-yl)amino]benzoic acid,
3-[(6-chloro-4-oxo-1,4-dihydroquinazolin-2-yl)amino]benzoic acid,
3-[(6-bromo-4-oxo-1,4-dihydroquinazolin-2-yl)amino]benzoic acid,
3-[(6-nitro-4-oxo-1,4-dihydroquinazolin-2-yl)amino]benzoic acid,
N-(4-oxo-1,4-dihydroquinazolin-2-yl)-beta-alanine,
N-(1-methyl-4-oxo-1,4-dihydroquinazolin-2-yl)-beta-alanine,
N-(1-allyl-4-oxo-1,4-dihydroquinazolin-2-yl)-beta-alanine,
N-(1-benzyl-4-oxo-1,4-dihydroquinazolin-2-yl)-beta-alanine,
N-(6-chloro-4-oxo-1,4-dihydroquinazolin-2-yl)-beta-alanine,
N-(6-bromo-4-oxo-1,4-dihydroquinazolin-2-yl)-beta-alanine,
N-(6-nitro-4-oxo-1,4-dihydroquinazolin-2-yl)-beta-alanine,
4-[(1-allyl-4-oxo-1,4-dihydroquinazolin-2-yl)amino]-2-chlorobenzoic acid, and
5-[(1-allyl-4-oxo-1,4-dihydroquinazolin-2-yl)amino]-2-chlorobenzoic acid.

3. A pharmaceutical composition which comprises a pharmaceutically acceptable carrier and a therapeutically effective amount of a compound according to claim 1.

* * * * *